United States Patent [19]

Rosenberg et al.

[11] Patent Number: 4,832,695
[45] Date of Patent: May 23, 1989

[54] TAMPER EVIDENT INJECTION SYRINGE

[76] Inventors: Bruce Rosenberg; Cynthia S. Rosenberg, both of 30 Glenridge Avenue, St. Catherines, Ont., Canada, L2R 4W6

[21] Appl. No.: 132,625
[22] Filed: Dec. 4, 1987

Related U.S. Application Data

[63] Continuation of Ser. No. 851,576, Apr. 14, 1986, abandoned.

[30] Foreign Application Priority Data

Sep. 23, 1985 [CA] Canada ................. 491356

[51] Int. Cl.⁴ ............................................. A67M 5/00
[52] U.S. Cl. ..................................... 604/111; 604/220
[58] Field of Search ............... 604/93, 110, 111, 218, 604/220–222, 227, 240, 241–243

[56] References Cited

U.S. PATENT DOCUMENTS

| 150,262 | 4/1874 | Slavin. | |
| 563,621 | 7/1896 | Schimmel | 604/241 |
| 715,290 | 12/1902 | Porter | 604/241 |
| 1,240,033 | 9/1917 | Dickinson et al. | 604/241 |
| 1,529,659 | 3/1925 | Marcy. | |
| 1,567,463 | 12/1925 | Platt et al. | 604/241 |
| 2,077,176 | 4/1937 | Lermer | 604/220 |
| 2,882,899 | 4/1959 | Nogier et al. | 604/222 |
| 3,135,260 | 6/1964 | Hamilton | 604/222 |
| 3,823,715 | 7/1974 | Holanek et al. | 604/218 |
| 3,874,383 | 4/1975 | Glowacki | 604/240 |
| 3,937,211 | 2/1976 | Merten | 128/2 |
| 4,026,287 | 5/1977 | Haller | 604/110 |
| 4,030,498 | 6/1977 | Tompkins | 604/221 |
| 4,531,940 | 7/1985 | Butterfield | 604/111 |
| 4,571,242 | 2/1986 | Klein et al. | 604/111 |

FOREIGN PATENT DOCUMENTS

| 872929 | 6/1971 | Canada | 128/88 |
| 925391 | 5/1973 | Canada | 128/84 |
| 1080571 | 7/1980 | Canada | 128/88 |

OTHER PUBLICATIONS

"Tip-Off Seals" Brochure by The West Company, Phoenixville, Pa. Bulletin Number A-7 (1 page).

Primary Examiner—Dalton L. Truluck
Assistant Examiner—Denise Whelton
Attorney, Agent, or Firm—Dority & Manning

[57] ABSTRACT

A tamper evident injection syringe of the disposable type is described having a container for storage of the material to be injected, means for expelling the material, an interference collar at one end of the container and a flange attached to the expelling means that is close fitting to the internal wall of the container and having a dimension greater than the interference collar such that the flange cannot pass through the interference means thereby preventing removal of the expelling means and the contents of the syringe. In addition a needle nub is described that permits connection of a needle or catheter and the connection of a tamper evident sealing cap that is easily removable yet when removed cannot be replaced without the removal being evident.

8 Claims, 1 Drawing Sheet

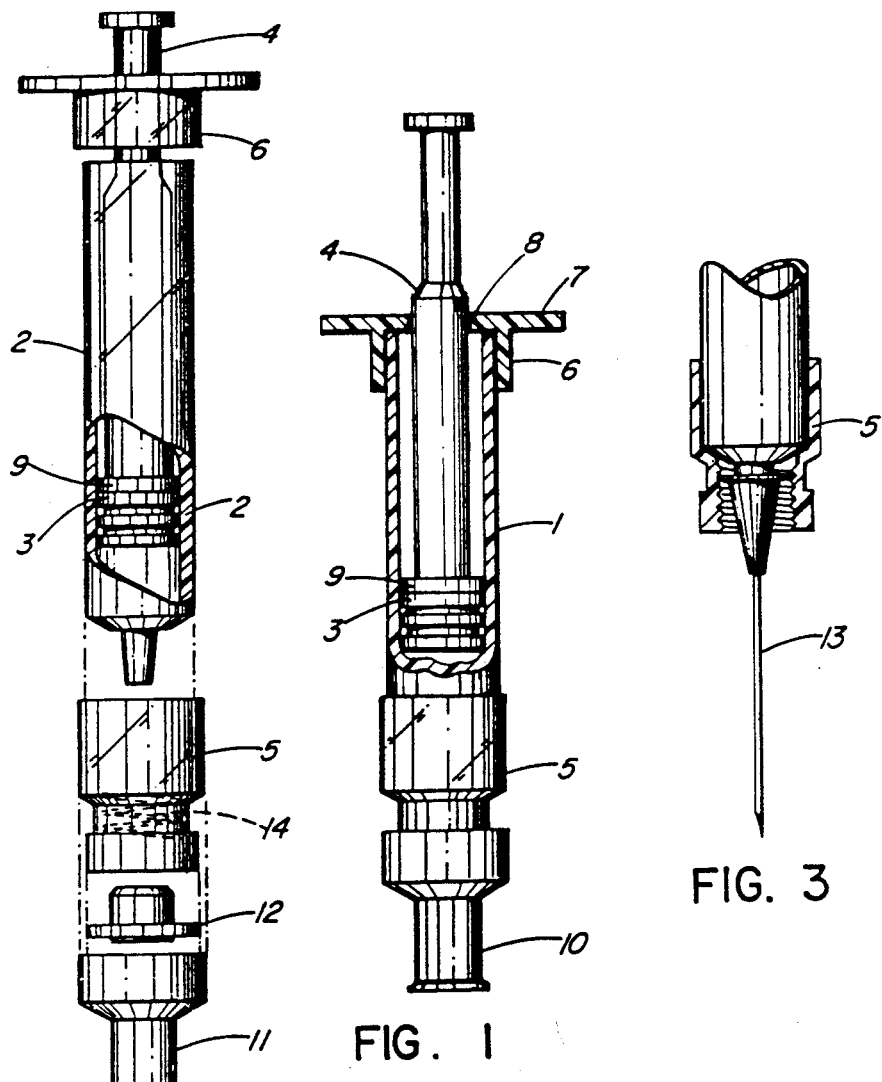

TAMPER EVIDENT INJECTION SYRINGE

This is a continuation of application Ser. No. 06/851,576, filed Apr. 14, 1986, which was abandoned upon the filing hereof.

BACKGROUND OF THE INVENTION

This invention generally relates to a disposable injection syringe of a type having a cylindrical container where the material to be injected is stored and having at one end a plunger/plunger rod combination and at the other end a needle nub to which in use the needle is attached. More specifically this invention relates to a syringe which is designed to prevent tampering of the contents by having an effective seal at the plunger end that would prevent tampering and at the needle or cap end having a easily removable cap though which once removed can not be reattached to the syringe without the tampering to the syringe and the contents being evident.

Injection syringes of both the disposable and reusable type have been in use for many years. All these syringes have the common features of a needle, container, plunger and plunger rod. Over the years variations and improvement have been introduced including quick attachment for needles or catheters and various designs of disposable storage ampules either being patient ready or requiring some assembly. All of the syringes suffer to a varying degree from a relatively new problem namely diversion and pilfering of medication or otherwise tampering with the contents of the syringe.

For disposable syringes, the contents are often packaged by the manufacturer and stored in the syringe until ready for use. As many of the syringes are packaged by the manufacturer, it is seldom possible to arrange for custom in hospital filling and packaging by the pharmacy of the hospital.

Current systems which depend on integrity of the packaging which surrounds the syringe to maintain the integrity of the contents of the syringe suffer from the inability to permit in hospital custom filling and capping while at the same time maintaining integrity.

Tampering and withdrawal of the contents of syringes is a current problem especially in high volume use situations, such as hospitals. Drugs that are stored in disposable syringes are often kept in security lockers either to prevent improper withdrawal of a prescription drug for non-prescription uses as well as to prevent intentional substitution of a drug for the prescribed drug. In numerous uses however, the drugs, while remaining secure while in the pharmacy of the hospital, may remain on the floor of the hospital for considerable periods of time where a number of people may gain access to the drugs before the drugs are actually used. Thus maintenance of the integrity of the contents of prepackaged disposable syringes is desirable.

Previous and current methods which are an attempt to solve this problem include specially designed packages which seal the entire syringe. One package is the Carpuject* cartridge needle units which are sealed in the factory in a plastic package. There is evidence of tampering if the plastic package has been torn open. Unless the syringe is used immediately after being removed from the plastic package there still remains the possibility of pilfering or tampering with the contents as the syringe can be pilfered by the insertion of needle through an exposed flexible rubber plunger. Furthermore the Carpuject* syringe has two parts which must be assembled before use. The first part consists of a cartridge which contains the needle, the rubber piston and

* trademark the storage ampule for the drug. The second part is a separate plunger injection system to which the cartridge is inserted. In this manner a Carpuject* syringe is not patient ready and must be assembled prior to use. In a similar manner, the Tubex* syringes have 2 parts which require assembly.

Another system for maintaining the integrity of the contents of a syringe through the use of packaging is the Min-i-ject* System manufactured by International Medication Systems of Almonte, Calif. The integrity of this contents is assured through the use of a plastic package though once the package is opened, the contents of the syringe are readily accessible by removing a replaceable cap and by insertion of a needle to penetrate the rubber plunger.

Other disposable syringes such as the Dupharject*, Kimble*, and Astra* all have removable plunger rods which permit access to the contents of the syringe by the insertion of a needle through the rubber plunger.

Other types of disposable syringes include the Hypod* Hypodermic syringe which is manufactured by Solo Pac Laboratories of Franklin Park, Ill. In this syringe both the plunger and needle ends are only protected by removable caps, which permit access to rubber plungers through which needles can be inserted.

SUMMARY OF THE INVENTION

Accordingly, the invention herein comprises a disposable injection syringe in which the contents of the syringe can not be tampered with or withdrawn without

* trademarks such tampering being evident. Further the design is such that in hospital custom filling is possible and once filled and capped the contents of the syringe are secure.

The invention comprises a disposable injection syringe with a cylindrical liquid storage container having at one end a needle nub to which can be attached an injection needle or a catheter and which in use has attached a tamper evident sealing cap which provides a sterile seal and which is easily removable to allow the attachment of the injection needle or catheter and having at the other end a plunger which is moveable within the container for expelling the material to be injected and a plunger rod attached to the plunger for moving the plunger and having an integral flange which is close fitting to the inside of the container and of a greater dimension than the inside dimension of a collar attached to the end opposite the needle such that in use the plunger rod cannot be removed from the cylinder and that the material to be injected can not be removed by the insertion of a needle through the plunger end.

The prevention of tampering at the end opposite the needle is achieved through the use of a flange on the plunger rod which is of a greater diameter than a collar which is attached to the end of the cylinder. The flange prevents accidental removal of the plunger assembly while at the same time prevents tampering of the contents or withdrawal of the contents of the syringe through the insertion of a needle through the resiliant rubber plunger.

The disposable injection syringe of this invention is also of a simple design such that there are no instructions and/or training that is required to use the syringe. The tamper evident sealing cap at the needle end is a known fixture in hospitals for use on serum finished vials though not with syringes. Furthermore the syringe of the present invention does not require any extra parts, packages, or assembly outside of attachment of a needle or catheter. Furthermore the simple design and use of the cap permits in hospital custom filling by addition of the liquid contents through the open needle end.

The resulting syringe prevents tampering in that at the plunger end access through the use of needles is not feasible while at the needle end any tampering is evident through the use of the sealing cap resulting in a disposable syringe which provides security and integrity while at the same time being of simple design.

BRIEF DESCRIPTION OF THE DRAWINGS

Details of preferred embodiments of the invention are described by reference to the accompanying drawings:

FIG. 1 is a side view, partially in section, of the injection syringe according to this invention without the needle or catheter being attached.

FIG. 2 is an exploded view showing the separate parts of the injection syringe shown in FIG. 1.

FIG. 3 is a side view, partially in section, of a complete injection syringe with the needle attached.

DETAILED DESCRIPTION OF PREFERRED EMBODIMENT

In the following descriptions, the corresponding elements as shown in each figure of the drawings are given the same reference number.

In FIG. 1 of the drawings the syringe indicated at 1 includes certain conventinal elements such as a metal, glass or plastic outer shell 2, a plunger 3, a plunger rod 4 at one end and a needle nub 5 at the other. In addition at the plunger end there is located a collar 6.

The collar 6 consists of a finger grip 7 as well as having an interior collar portion 8.

The plunger rod has adjacent the plunger a circumferential flange 9 which is of a diameter greater than the inside diameter of the collar flange 8 that in use prevents the plunger rod from being withdrawn. By necessity the difference in diameters need only be of sufficient extent to prevent removal of the piston from the syringe. In addition the circumferential flange 9 must be close fitting with the interior of the container 2 to prevent insertion of a needle between the flange and the inside of the cylinder.

The plunger 3 and the plunger rod 4 may be permanently affixed to one another or alternatively may be attached by a screw which permits the plunger rod to be removable from the plunger. Even though the plunger may be removable from the plunger rod, neither plunger rod nor the plunger can be removed from the container by reason of the collar 6 and flange 9.

The collar 6 can be attached to the cylinder through the use of cement, a snap fit or alternatively may be an integral part of the container.

The interior collar portion 8 of the collar 6 can also be a split collar designed to slip around the plunger rod 4 prior to its insertion into the mouth of the barrel. Once inserted the split collar can be attached. Use of a split collar permits the thumbrest on the plunger rod 4 to be larger and the finger grips 7 to be an integral part of the barrel.

The plunger 3 is preferrably a Teflon* faced syringe plunger of the type manufactured by the West Company (Teflon is a registered trademark of E. I. Dupont de Nemours and Company Inc.) Teflon faced rubber plungers provide a relatively inert substance which also follows the contours of the surface to and around the periphery of the plunger. When the Teflon coated plunger is inserted in the container the outer diameter of the plunger is slightly larger than the inner diameter of the vial resulting in a compressive force which makes the Teflon contact the glass container. The uncoated surface of the plug is an effective sealing contact with the vial or container. The Teflon face syringe plunger may have on the plunger rod side recess grooves which are adapted to accept a screw from the plunger rod.

The needle nub 5 can also be an integral part of the syringe cylinder or alternatively may be glued or otherwise fused to the cylinder. At the needle end of the nub there are located means for attaching a needle or a catheter to the inside portion of the needle nub. The outside of the needle nub is designed to receive the cap 10 which is composed of two parts, an aluminium top half closure 11 and a rubber stopper or liner 12. This cap are available from the West Company of Phoenixville, Pa. U.S.A. and are sold as Tip Off* seals. When the cap 10 is tipped off in use, the rubber seal 12 is automatically removed which avoids contact with the vials or cylinders mouth by the users hand, and the aluminum top 11 is irreversibly deformed as understood by those of ordinary skill in the art. The one step removal of the stopper and seal makes the cap quick to open and easy to use. Once the seal has been taken off signs of tampering are evident due to the deformation of the aluminum top 11. Hence, the cap 10 cannot be reattached to the syringe without the prior removal being evident.

The Tip Off* cap can be applied to the syringe using a rotary type screw feed West capper model RW-600*

---

* trademarks or a manually operated capper. One standard size for the tip off seal is the 13 millmeter size seal.

Tip off seals are commonly used in hospital settings for serum finished vials though have not been used with syringes. Because of the familiarity with tip off seals in the hospital setting, no instruction would be required to educate users of the syringe as to the manner of removing the seal.

FIG. 3 shows a syringe after the cap has been removed and a needle 13 has been attached. Attachment of the needle is achieved by screwing the needle with a needle shield attached onto the screw threads 14. The screw threads are located on the inside wall of the needle nub 5.

The needle attachment method is preferably the luer-lock* system which results and insures a tight and secure fit of the needle or tubing for the injection.

The sterile disposable needles can be of the type commercially available from B-D Yale*, though any type of quick attachment needle would be suitable.

The syringe would be assembled first of all by insertion of the plunger and plunger rod into the cylinder and then by attachment of the collar 6 and the needle nub 5.

The drug to be administered can be either be packaged at the pharmaceutical manufacturers' facilities or alternatively may be filled in a hospital pharmacy.

If the drug is packaged with the syringe at the pharmaceutical manufacturers' facilities, automative machinery can be used to insert the drug through the

* trademarks needle opening end 15 followed by automated capping by attachment of the cap 10. The syringe in this form is in a sterile sealed environment which can be then readily packaged and distributed until required to be used, at which time the cap is tipped off, the needle inserted and then immediately injected.

Alternatively a pharmacy can obtain empty syringes consisting of the needle nub 5, the cylinder 2, the plunger 3, plunger rod 4 and collar 6. The syringe can be filled with a specific drug on a custom basis that is required for use in the hospital with the use of vial filling apparatus. Hand-capping machinery is available that would permit a cap 10 to be applied in the pharmacy of the hospital resulting in a syringe that will remain integral until the syringe is used.

The resulting syringe is of such a design that easy and visible aspiration is possible where the syringe is plastic or glass. The preferable material for the cylinder is glass made of a type 1 bora silicate glass which has strength, transparentcy and inertness.

In addition the plunger rod 4 can be optionally tapered to permit easy handling during aspiration. Disclosed in the drawings is a ribbed type plunger rod, though the plunger rod could optionally be a solid cylindrical type which is designed to be close fitting to the interior of the collar 8 to further prevent insertion of a needle and thus to maintain the integrity of the contents of the syringe.

The flange 9 while primarily present to prevent tampering also provides greater stabilization of the plunger during injection.

A further method of use of the syringe is where the contents of the syringe are not added to the patient through a needle but rather a cathater is used. The luer-lock* system permits application of a either a needle or a cathater to the syringe providing additional flexability in the use of this product.

* trademarks

The embodiments of the invention in which a exclusive property or privilege is claimed are defined as follows:

1. A unitary tamper evident syringe, comprising:
   an elongated cylindrical container for storing material in an interior chamber thereof to be injected into a subject having a plunger end adapted for the passage of a plunger rod therethrough and having a needle end with attachment means;
   said attachment means comprising a needle nub fixedly secured at a first end on said needle end of said container, said nub having a generally cylindrical construction of about the same diameter as that of the container and fitted thereon, and having on a second end thereof interiorly-defined receiving means said nub removably supporting tamper evident closure means, upon removal of said closure means said nub adapted to removably receive on the second end one of an injection needle and catheter for passage therethrough of the material being expelled from the syringe, said nub further having exteriorly-defined mounting means adjacent the second end including a circumferential rib, said closure means received on said rib, said closure means of the type comprising a flexible plug and a deformable metallic exterior mounted about said rib and which cannot be re-affixed to said attachment means as originally mounted once removed therefrom, whereby tampering of said closure is indicated;
   interference means, fixedly secured to said plunger end, including a collar for engaging said cylindrical container plunger end for securement thereto, and including a relatively planar, rigid annular element forming part of said collar, said rigid annular element positioned at said plunger end for reducing the diameter of the passage therethrough; and
   plunger means reciprocally received within said container for controllably expelling fluid within said chamber outwardly through said needle end of said container, said plunger means including a plunger rod and a plunger element having a close fit to the interior of said container and received on the end of said plunger rod;
   said plunger rod extending outwardly of said container through said plunger end with a close fit to the reduced diameter thereof;
   said plunger means further includes a rigid flange, received about said plunger rod interposed between said plunger element and said interference means, and having a relatively close fit with the interior chamber of said container to prevent insertion of a needle into the interior chamber of said container through said open plunger end thereof, whereby said rigid flange engages the reduced diameter passage defined by said interference means at said plunger end as said plunger means is moved in a direction to withdraw same from said container so as to affirmatively prevent intentional removal of said plunger means from said container, wherefore damage to any of the foregoing elements or defeat of said interference means evidence tampering of said unitary syringe.

2. A syringe as in claim 1 wherein said rigid flange forms a part of said plunger rod.

3. A syringe as in claim 2 wherein said collar has an external extension which defines a finger grip for a user of said syringe.

4. A syringe as in claim 2 wherein said collar includes a split ring assembly received about said plunger rod.

5. A syringe as in claim 1, wherein said receiving means includes screw threads located on an inside wall of said attachment means.

6. A syringe as in claim 1, wherein said circumferential rib includes a radial projection located about said attachment means on said second end thereof.

7. A syringe as in claim 1, wherein said attachment means is formed as an integral part of said container.

8. A syringe as defined in claim 1, wherein said collar comprises a cylindrical extension member which engages the outside diameter of said cylindrical container plunger end for securement thereto.

* * * * *